(12) United States Patent
Sakakibara et al.

(10) Patent No.: US 6,982,325 B1
(45) Date of Patent: Jan. 3, 2006

(54) GENE ENCODING PROTEIN HAVING AURONE SYNTHESIZING ACTIVITY

(75) Inventors: Keiko Sakakibara, Muko (JP); Yuko Fukui, Osaka (JP); Yoshikazu Tanaka, Otsu (JP); Takaaki Kusumi, Suita (JP); Masako Mizutani, Kyoto (JP); Toru Nakayama, Sendai (JP)

(73) Assignees: Suntory Flowers Limited, Tokyo (JP); Suntory Limited, Osaka (JP)

( * ) Notice: Subject to any disclaimer, the term of this patent is extended or adjusted under 35 U.S.C. 154(b) by 0 days.

(21) Appl. No.: 09/446,089

(22) PCT Filed: Apr. 16, 1999

(86) PCT No.: PCT/JP99/02045

§ 371 (c)(1),
(2), (4) Date: Dec. 17, 1999

(87) PCT Pub. No.: WO99/54478

PCT Pub. Date: Oct. 28, 1999

(30) Foreign Application Priority Data

Apr. 17, 1998 (JP) .................................. 10/107296

(51) Int. Cl.
*C07H 21/04* (2006.01)
(52) U.S. Cl. ................. 536/23.1; 536/24.3; 536/24.33; 435/320.1; 435/69.1; 435/252.3; 435/410
(58) Field of Classification Search ............... 536/23.1, 536/24.3, 24.33; 435/320.1, 69.1, 252.3, 435/410
See application file for complete search history.

(56) References Cited

U.S. PATENT DOCUMENTS 6,242,221 B1 * 6/2001 Robinson ................... 435/91.2

FOREIGN PATENT DOCUMENTS

JP 7-501686 2/1995
WO 96/40951 * 12/1996

OTHER PUBLICATIONS

Hunt et al. (Plant molecular biology: an international journal on molecular biology, biochemistry and genetic engineering, Jan 1993. vol. 21, No. 1, pp. 59-68).*
Kupper et al. (The Journal of Biological Chemistry, 1989, vol. 264, No. 29, p. 17250-17258).*
Esaka, M. et al., "Molecular cloning and nucleotide sequence of full-length cDNA for ascorbate oxidase from cultured pumpkin cells", Eur. J. Biochem. (1990). p. 537-541.
Shahar, T. et al., "The Tomato 66.3-kD Polyphenoloxidase Gene: Molecular Identification and Developmental Expression", The Plant Cell, vol. 4, No. 2, p. 135-147 (1992).
Joy, R. W. et al., "Cloning and Characterization of Polyphenol Oxidase cDNAs of Phytolacca americana", Plant Physiol., vol. 107, No. 4, p. 1083-1089 (1995).
Paul K. Boss et al, "An apple polyphenol oxidase cDNA is up-regulated in wounded tissues," Plant Molecular Biology, vol. 27, pp. 429-433, 1995.
Toru Nakayama et al, "Specificity analysis and mechanism of aurone synthesis catalyzed by aureusidin synthase, a polyphenol oxidase homolog responsible for flower coloration," FEBS Letters, vol. 499, No. 1-2, pp. 107-111, 2001.
T. Nakayama et al, "Aureusidin Synthesis: A Polyphenol Oxidase Homology Responsible for Flower Coloration," Science, vol. 290, pp. 1163-1166, 2000.
Takuya ato et al, "Enzymatic formation of aurones in the extracts of yellow snapdragon flowers," Plant Science, vol. 160, No. 2, pp. 229-236, 2001.

* cited by examiner

*Primary Examiner*—Juliet C. Switzer
(74) *Attorney, Agent, or Firm*—Burns, Doane, Swecker & Mathis, L.L.P.

(57) ABSTRACT

The present invention provides a protein having aurone synthase activity involved in the color of flowers such as snapdragons, a gene that encodes it, cDNA in particular, and its applications. This gene can give yellow color to the flowers of plants by introducing into plants deficient in chalcone isomerase and so forth and expressing.

8 Claims, 6 Drawing Sheets

Leaf Stem Bud Petal

← 3.4kb

← 1.8kb yellow pink white

← 3.4kb

← 1.8kb

Amount of anti-SYP8-Sepharose 4B added

| 0 μl | 200 μl | 500 μl | 815 μl |

Aurone Synthase →

GENE ENCODING PROTEIN HAVING AURONE SYNTHESIZING ACTIVITY

FIELD OF THE INVENTION

The present invention relates to genes encoding proteins having activity that synthesizes aurones by using chalcones as substrates, and its utilization. More specifically, the present invention relates to genes encoding polyphenoloxidases having activity that synthesizes aurones by using chalcones as substrates, and its utilization. More specifically, the present invention, for example, relates to genes encoding proteins derived from snapdragons having activity that synthesizes aurones by using chalcones as substrates.

BACKGROUND ART

The flower colors of orange, red, violet and blue primarily are provided by flavonoids referred to as anthocyanins. Although yellow is mainly provided by compounds other than flavonoids, such as carotenoids, betalains, etc., the yellow color of some plants is provided by flavonoids. For example, compounds classified as aurones are known to be present in the petals of some varieties of snapdragon, limonium, morning glory, dahlia, strawflower, Jerusalem artichoke and cosmos (Saito: BIO HORTI 1, 49–57, 1990).

Known examples of aurones include 4',6-dihydroxyaurone, 4,4',6-trihydroxyaurone, aureusidin, sulfretin and bracteatin, with aureusidin and bracteatin being contained in snapdragon, aureusidin contained in limonium, aureusidin contained in morning glory, sulfretin contained in dahlia, bracteatin contained in strawflower, and sulfretin contained in Jerusalem artichoke.

In addition, aurones are known to be contained in the plant of the family Compositae including the genera *Coreopsis, Helianthus, Tithonia, Zinnia* and *Viguiera*; the family Ericaceae including the genus *Vaccinium*; the family Cyperaceae including the genus *Cyperus*; the family Leguminosae including the genera, *Acacia, Pterocarpus* and *Soja*; and the family Rubiaceae including the genus *Mussaenda* (The Flavonoids, edited by J. B. Harbone, 1988, Chapman & Hall, 340–342).

The synthesis pathway of anthocyanins has been extensively researched, and with respect to the biosynthesis of aurones, it has been suggested based on its structure that 4',6-dihydroxyaurone is synthesized from 2',4,4'-trihydroxychalcone, and it has been proposed that peroxidase is involved in that reaction (Rathmel and Bendall, Biochem. J. 127, 125–132, 1972). However, there are no examples of definitively measuring the biosynthesis reaction of aurones using petal extracts and so forth of plants, and there are no reports that clarify the manner in which the reaction occurs in plant petals. In addition, there are also no reports of purifying enzymes involved in aurone synthesis.

DISCLOSURE OF THE INVENTION

Therefore, the inventors of the present invention have attempted to clarify the biosynthesis mechanism of aurones to provide a means for controlling the color of plants, and particularly their flowers.

The inventors of the present invention established an assay method for measuring the reaction by which aurones are synthesized from chalcones using a crude extract of snapdragon petals containing aurones. The aurones produced at this time are not 4',6-dihydroxyaurone considered in the prior art, but rather aureusidin, and this reaction that can now be measured has not been previously known. In addition, an enzyme (aureusidin synthase) that synthesizes aurones (aureusidin) by using chalcones as substrates from the petals of snapdragons was purified by electrophoresis to a single band, by using the assay method. The biochemical properties of this enzyme were identified using this pure standard. In addition, the partial amino acid sequences of this enzyme were also determined. A gene for this aurone synthase, which synthesizes aurones by using chalcones as substrates, was obtained from a cDNA library prepared from the petal of snapdragon, based on the partial amino acid sequences as described above.

Note that known examples of chalcones include, but not restricted to tetrahydroxychalcone, pentahydroxychalcone, butein and 2',4,4'-trihydroxychalcone.

On the other hand, the resulting gene has homology in the copper binding region, which is the active center of polyphenol oxidase. Therefore, it was confirmed whether tyrosinase, which is known as a kind of polyphenol oxidases, has activity to synthesize aurones from chalcones or not, and as a result, tyrosinase was also clearly shown to have activity to synthesize aurones.

Thus, the present invention provides genes encoding proteins having activity to synthesize aurones by using chalcones as substrates. Moreover, it provides genes encoding polyphenol oxidase having activity to synthesize aurones by using chalcones as substrates. Moreover, it provides a gene encoding a protein having activity to synthesize aurones by using chalcones as substrates, and having the amino acid sequence shown in SEQ ID NO. 2. The present invention also provides a vector containing the above-mentioned gene.

Moreover, the present invention provides a host transformed by the above-mentioned vector. This host may be a microorganism, plant cells or animal cells, or it may be a plant.

The present invention also provides a process for production of an aurone synthase such as aureusidin synthase, characterized by culturing the above-mentioned cells or cultivating the above-mentioned plant. The formed enzyme can be recovered, or be made to function to regulate the color tone in a plant. In this case, aurones are synthesized by enzyme formed in the plant, and these aurones then regulate the color of the plant such as its petals.

Thus, the present invention also provides a method for regulating the flower color of plants characterized by introducing a gene for an enzyme such as aureusidin synthase having activity to synthesize aurones by using chalcones as substrates into a plant or plant cells to express above-mentioned gene, and by synthesizing aurones in a plant by the enzyme formed. The present invention also provides a plant in which flower color is regulated in this manner.

The present invention also provides a method of synthesizing aurones characterized by allowing the above-mentioned enzyme protein to act on chalcones serving as the substrate pigment.

The present invention also provides an enzyme protein encoded by the above-mentioned gene.

BRIEF DESCRIPTION OF THE DRAWINGS

Petal stage 1: Bud petal length up to 1 cm
Petal stage 2: Bud petal length 1 to 1.5 cm
Petal stage 3: Bud petal length 1.5 to 2.0 cm
Petal stage 4: Bud petal length 2.0 to 2.5 cm
Petal stage 5: Bud petal length 2.5 to 3.0 cm
Petal stage 6: Blossomed petal 3.0 cm or more

EMBODIMENT FOR CARRYING OUT THE INVENTION

Figure 1:
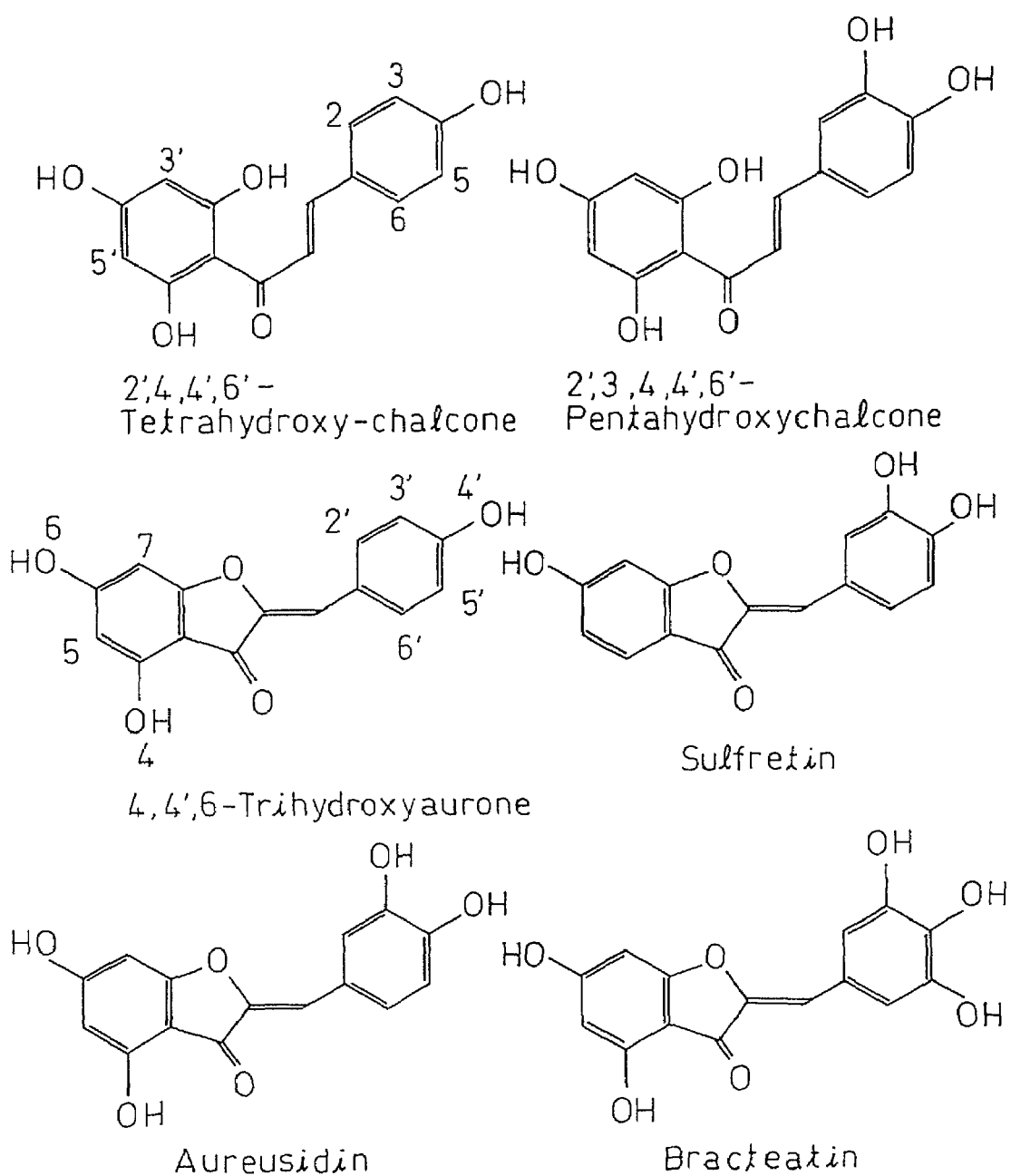
FIG. 1 shows the structural formulas of aurones and chalcones.
Figure 2:
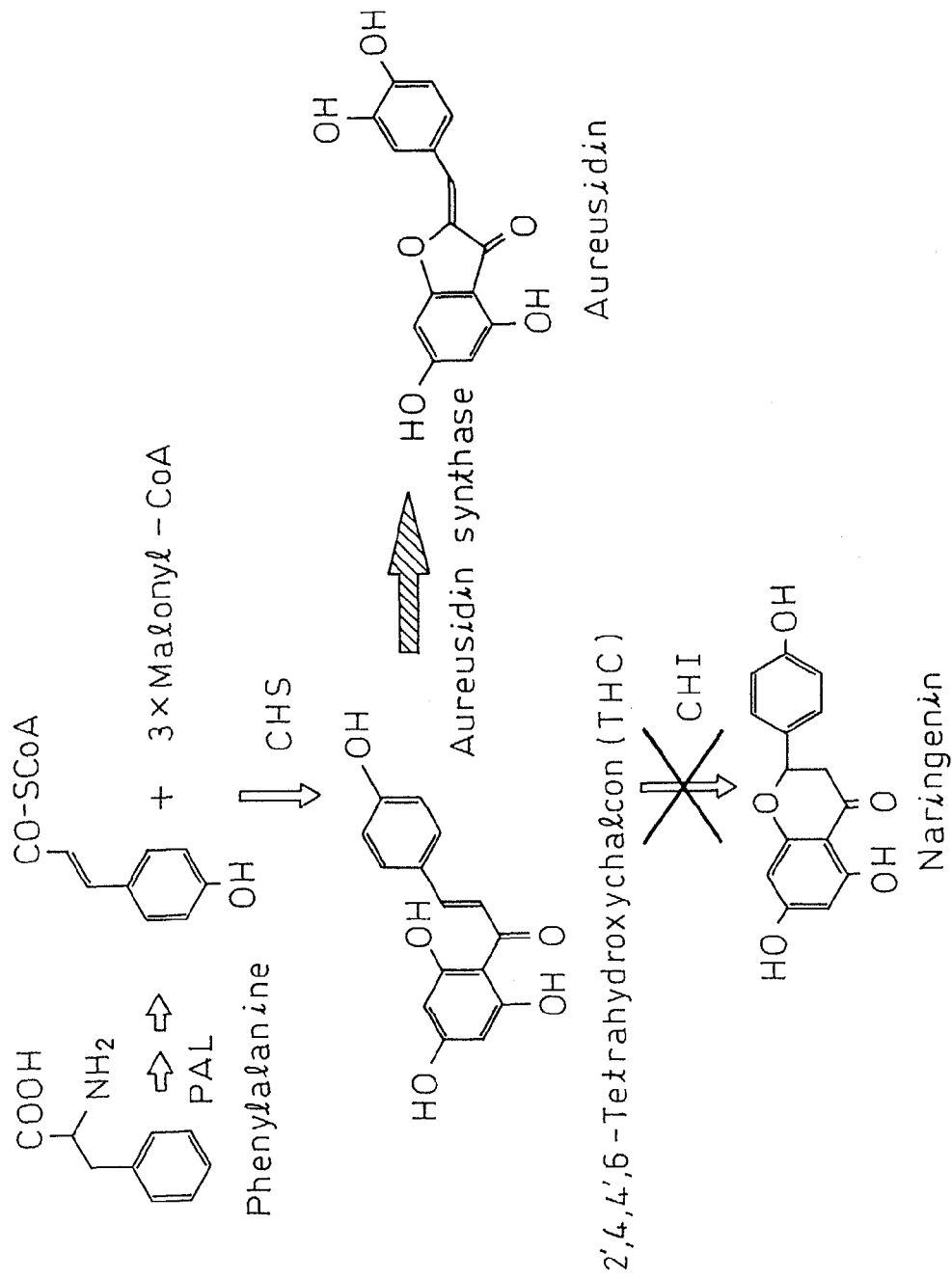
FIG. 2 shows the biosynthesis pathway of aurones.

To begin with, aureusidin synthase is purified by various chromatography methods from the petals of yellow snapdragon. Next, partial amino acid sequences of aureusidin synthase are analyzed in accordance with a conventional method to prepare synthetic oligonucleotides encoding these amino acid sequences.

On the other hand, Poly A+RNA is prepared from the same snapdragon petals, and cDNA library is prepared in accordance with a conventional method.

PCR is carried out using the above-mentioned synthetic nucleotides using cDNA of yellow snapdragon petals as a template to acquire a DNA fragment specific to aureusidin synthase. This DNA fragment is subcloned in a vector to prepare a plasmid.

The above-mentioned cDNA library is screened using an inserted DNA contained in the above-mentioned plasmid to obtain a clone. The plasmid derived from this clone is then isolated followed by determination of the nucleotide sequence.

The protein having the enzyme activity has a region essential for an enzyme activity, and a region not essential for enzyme activity. It is known that enzyme activity is maintained even if the non-essential region is modified by removal (deletion) or addition of one or more amino acids and/or substitution by other amino acids. Thus, the present invention includes not only a protein having the amino acid sequence shown in SEQ ID NO. 2, but also proteins having an amino acid sequence modified by removal, deletion or addition of one or more amino acids and/or one or more substitutions by other amino acids in the amino acid sequence shown in SEQ ID NO. 2 while maintaining the activity to synthesize aurones by using chalcones as substrates, as well as genes encoding the proteins.

Moreover, cases are known in which a protein having identical enzyme activity may have a different amino acid sequence due to an allelic variation. Moreover, it is also known that enzymes having identical or equivalent enzyme activity are distributed over numerous species, and that these enzymes have a high degree of homology of their amino acid sequences. Genes encoding these proteins can be selected by hybridization with a gene of the present invention. Thus, the present invention also includes a gene that hybridizes with nucleic acid having the nucleotide sequence shown in SEQ ID NO. 1 under a stringent condition and that encoding a protein having the activity to synthesize aurones by using chalcones as substrates, and a protein encoded by the gene.

The gene that hybridizes with nucleic acid having the nucleotide sequence described in SEQ ID NO. 1 and that encoding a protein having enzyme activity to synthesize aurones by using chalcones as substrates may be an artificially modified form or naturally-occurring form of a gene that encodes the amino acid sequence described in SEQ ID NO. 2. Examples of naturally-occurring genes include cDNA or genomic DNA obtained from plants having aurone synthase such as snapdragon, limonium, morning glory, dahlia, strawflower and Jerusalem artichoke. The stringency for hybridization is, for example, 5×SSC at 50° C., preferably 2×SSC at 50° C., and more preferably 0.2×SSC at 50° C.

It is well known that there are many cases in which protein, having an amino acid sequence with a high degree of identity relative to a native amino acid sequence of a protein having enzyme activity, has enzyme activity that is similar to that of a native protein. Thus, the present invention also includes proteins having activity to synthesize aurones by using chalcones as substrates and having an amino acid sequence having amino acid sequence identity of 55% or more, preferably 60% or more, preferably 70% or more, more preferably 80% or more and particularly preferably 90% or more relative to the amino acid sequence shown in Sequence ID No. 2, and a gene encoding that protein.

It is also known that enzymes having equivalent enzyme activity may have common epitopes in many cases. Thus, the present invention also includes the above-mentioned various proteins having aurone synthesis activity, and particularly proteins having activity that synthesizes aurones by using chalcones as substrates, which also specifically bind with an antibody against the protein having the amino acid sequence shown in SEQ ID NO. 2, and a gene encoding that protein.

In the present invention, a gene that encodes protein having the amino acid sequence shown in SEQ ID NO. 2 can be obtained from snapdragon as cDNA or genomic DNA. A method for cDNA cloning is specifically described in Examples 8 through 10. In order to obtain a genomic DNA, a genomic DNA library is prepared from snapdragon in accordance with a conventional method, and this is then screened in accordance with a conventional method by cDNA or its fragment.

In the present invention, a gene that encodes a protein having a modified amino acid sequence relative to the amino acid sequence in SEQ ID NO. 2 can be prepared by modifying the nucleotide sequence of DNA such as cDNA that encodes protein having the amino acid sequence shown in SEQ ID NO. 2 in accordance with a conventional method to manipulate the gene by site-directed mutagenesis, PCR and so forth.

Naturally-occurring genes, that hybridize with nucleic acid having the nucleotide sequence described in SEQ ID NO. 1 and that encodes an enzyme having activity to synthesize aurones by using chalcones as substrates, are obtained by preparing a cDNA library or genomic DNA library from a plant which has ability to produce a protein having aurone synthase activity in accordance with a conventional method, and then screening the library by using, for example, cDNA or its fragment having the nucleotide sequence shown in SEQ ID NO. 1 as a probe. The above-mentioned conditions can be used for the hybridization at this time.

In addition, the aurone synthase obtained from snapdragon is a kind of polyphenol oxidase, therefore the inventors of the present invention, considering that other polyphenol oxidases also have activity to synthesize aurones from chalcones, examined whether an enzyme sold commercially as tyrosinase, a polyphenol oxidase derived from Neurospora, has aurone synthesis activity or not. As a result, the tyrosinase was determined to have aurone synthesis activity. Consequently, enzymes having polyphenol oxidase activity clearly have activity to synthesize aurones by using chalcones as substrates.

Although the physiological role of enzymes having polyphenol oxidase activity is not yet clear, they are primarily classified into three types which are catechol oxidase (enzyme no. 1.10.3.1), laccase (enzyme no. 1.10.3.2.) and tyrosinase (enzyme no. 1.14.18.1), and are classified with different enzyme numbers according their substrate specificity. They are copper enzymes in which copper is present in the enzyme reaction center, and high dimensional structures of proteins, etc. are thought to be a cause of substrate specificity.

In this manner, since a conserved region corresponding to the copper-binding region is present in polyphenol oxidase, polyphenol oxidase gene can be obtained according to an established method such as PCR with a primer based on the amino acid sequence of this region (Plant Physiol., Vol. 107, pp. 1083–1089, 1995; Plant Physiol., Vol 109, pp. 525–531, 1995), and a gene encoding a protein having activity to synthesize aurones can be obtained from the gene obtained as described above.

The present invention also provides a process for production of the above-mentioned proteins having activity to synthesize aurones by using chalcones as substrates. This method is characterized by introducing a vector containing a DNA encoding the above-mentioned protein into a host, culturing or growing said host, and collecting the above-mentioned protein as desired. The host may be host cells or plants or other organisms. Examples of host cells include procaryotic cells and particularly bacterial cells such as those of *Escherichia coli*, and the genus *Bacillus* including the species *Bacillus subtilis* and *Bacillus brevis*, and lower eucaryotes, including fungi such as yeasts like the genus *Saccharomyces* such as the species *Saccharomyces cerevisiae*, or molds like the genus *Aspergillus* such as the species *AsperQillus oryzae* and *Aspergillus niger*.

Moreover, examples of higher eucaryotic cell hosts include insect cells such as silkworm cells, animal cells such as CHO cells, and human cultured cells such as HeLa cells.

The gene described in the present invention can also be expressed in organisms such as animals and plants. A detailed description of expression in plants is provided below.

A vector, and particularly an expression vector, containing DNA of the present invention contains an expression control region, and this expression control region is dependent on the host cells. For example, trc promoter, tac promoter, lac promoter or T7 promoter can be used for the promoter of a bacterial expression vectors. Examples of promoters of a yeast expression vector that can be used include promoters of glycolytic enzyme genes such as glycerolaldehyde-3-phosphate dehydrogenase promoter and galactokinase promoter. In addition, virus promoters can be used as a promoter of animal cell expression vectors.

Conventional means used to isolate and purify proteins, such as liquid chromatography and affinity chromatography, can be used to recover a protein having an activity to synthesize aurones from a culture by using chalcones as substrates. Affinity chromatography can be performed using the specific binding with antibody, for example antiserum or monoclonal antibody, against protein having aurone synthase activity of the present invention.

Antiserum (polyclonal antibody) to protein having aurone synthase activity described in the present invention can be produced by immunizing an animal such as a rabbit with protein described in the present invention, such as the protein obtained in Example 4, together with adjuvant, and obtaining serum from the animal. Monoclonal antibody can be produced by immunizing an animal such as a mouse against, for example, a protein described in the present invention in accordance with a conventional method, and fusing the B lymphocytes, such as spleen cells, obtained from a mouse, with mouse myeloma cells to obtain a hybridoma, followed by culturing that hybridoma.

Based on the current level of technology, if the cDNA can be put under the control of a constitutive or inducible promoter, and introduced into a plant such as petunia, rose, carnation, chrysanthemum, torenia, verbena, gerbera, tobacco, strawberry, Jerusalem artichoke, gentian, gladiolus or tulip, using *Agrobacterium*, a particle gun or electroporation, the aurone synthase gene can be expressed in a petal and so forth.

It is predicted that aurones are synthesized in petals where aurone synthase is expressed, which cause the yellow color of the petals. Plants obtained in this manner are able to provide new colors of flowers that do not exist for conventional varieties. In addition, some of plant species having yellow color contain carotenoids (chrysanthemums and roses) or betalain (cactus), but the tone of these yellow colors are different from those by aurones. Therefore, the present invention is also useful in enlarging the spectrum of color tones of plant species already having yellow color.

Some snapdragons having yellow flowers are deficient in chalcone isomerase activity and have aurone synthase. Since chalcone isomerase acts competitively with aurone synthase, naringenin is formed from tetrahydroxychalcone in the presence of chalcone isomerase, and this ultimately becomes anthocyanin and flavone. Thus, when producing aurones by expressing aurone synthase gene in plants, it is preferable that the plant be deficient in chalcone isomerase.

In general, it is possible to artificially suppress the activity of plant genes, and there are numerous known examples of suppressing genes involved in flavonoid synthesis in particular. An antisense method and a cosuppression method are used to artificially suppress gene expression, and genes involved in flavonoid synthesis have been found to be able to be suppressed by either of these methods (van der Krol, et al., Nature (1988) 333, 866–869; Napoli, et al., Plant Cell (1990) 2, 279–289). It is also possible to suppress expression of chalcone isomerase gene in the same way.

Chalcone isomerase gene has already been obtained from plant species, such as petunia, alfalfa, snapdragon, apple, kidney bean and grape (Holton, et al., Plant Cell (1995) 7, 1071–1083). Comparison of the amino acid sequences of these chalcone isomerases reveals that the sequence is well conserved among species. There are many examples that genes involved in flavonoid synthesis can be easily cloned by using a corresponding gene derived from another plant as a probe. Alternatively, cloning can also be performed by PCR using a conserved region of known genes or amino acid sequences compared with each other. Thus, chalcone isomerase gene can be easily obtained from any plant species (Gutterson, Hort. Sci., Vol. 30, pp. 964–966, 1995).

In addition, similar effects can be expected by suppressing gene expression of flavanone-3-hydroxidase or dihydroflavonol-4-reductase. Since these enzyme genes have also been obtained from numerous plant species (Gong, et al., Plant Mol. Biol., 35, pp. 915–927, 1997), they can be obtained from any plant species by using a method similar to the case of chalcone isomerase.

Thus, in order to breed a certain plant species having yellow flowers provided by aurones, the aurone synthase gene should be expressed in the petals. Preferably, the aurone synthase gene should be expressed while suppressing the expression of chalcone isomerase gene. In this case, the promoters used to regulate expression of these genes may be constitutional promoters or petal-specific promoters. More preferably, these techniques allow to obtain flowers with stable yellow color in combination with introduction of a glycosyltransferase gene that adds a sugar to the aurone. These techniques are possible with the current level of technology.

Furthermore, in dahlia and snapdragon, flower color is known to become brown when both anthocyanins and aurones are present. It is possible to breed brown flowers by introducing aurone synthase into a plant that produces anthocyanins in its flowers. Such flowers are also industrially important as a new color of flowers.

EXAMPLES

The following provides a detailed description of the invention through its examples.

Example 1

Preparation of Tetrahydroxychalcone 20 ml of 50% (v/w) potassium hydroxide were added to 4 g of naringenin and completely dissolved. After holding this solution at 100° C. for 90 seconds, the solution was immediately diluted and cooled with 300 ml of ice water to stop the reaction. Next, 6 N hydrochloric acid was added to this solution in a draft chamber to lower the pH to 3 or lower and form a precipitate. The resulting yellow precipitate was filtered out of solution and dissolved in a minimum amount of ethanol, followed by the addition of 400 ml of cold water a little at a time while cooling over ice. After allowing to stand overnight, the precipitate obtained by centrifuging at 8000 rpm for 30 minutes was resuspended in water and freeze-dried. The weight of crude tetrahydroxychalcone (THC) after freeze-drying was 2.7 g.

The crude THC was dissolved in a minimum amount of methanol, and the THC was purified by reverse phase high-performance liquid chromatography. The THC was developed using the Shimakyuu YMC D-ODS-5 S-5 120A (2.0 cm×25 cm) at a flow rate of 4.5 ml/min in an aqueous solution of 40% (v/v) acetonitrile and 0.03% (v/v) trifluoroacetic acid. THC was eluted at about 25 minutes, while naringenin was eluted at about 29 minutes. The THC fractions were collected and freeze-dried. Chromatography was repeated once under the same conditions to obtain purified THC.

Example 2

Preparation of Aureusidin 290 g of the petals of snapdragon cultivar Butterfly Yellow were crushed in liquid nitrogen and soaked overnight in 2 liters of 50% acetonitrile containing 0.1% TFA. After filtering through diatomaceous earth and concentrating the filtrate under reduced pressure, the concentrate was purified with HP-20. The yellow pigment fraction was concentrated and applied to a separation HPLC. Using water as solution A and 0.1% TFA in 50% acetonitrile as solution B, chromatography was performed using the Shimakyuu YMC D-ODS-5 S-5 120A (2.0 cm×25 cm) under gradient condition of 120 minutes at a linear concentration gradient from 20% B to 60% B. As a result, bracteatin-6-glucoside was eluted at 40 minutes, aureusidin-6-glucoside was eluted at 53 minutes, and tetrahydroxychalcone-4-glucoside was eluted at 100 minutes. The resulting aureusidin-6-glucoside was hydrolyzed with β-glucosidase to obtain aureusidin.

Example 3

Measurement Method of Aurone Synthase Activity

The reaction was started by adding 5 μl of THC, having an absorbance of 462 at 366 nm in ethanol, to 50 μl of 1 M sodium acetate buffer (pH 5.0) and 350 μl of crude enzyme solution diluted with water. After allowing to react for 1 hour at 30° C., and adding 100 μl of an aqueous solution of 90% (v/v) acetonitrile containing 1% (v/v) TFA to stop the reaction, activity was measured by HPLC. The crude enzyme solution in each purification step described later in Example 4 was measured.

The YMC J'Sphere ODS M80 column (4.6×150 mm) was used and the flow rate was set at 0.7 ml/min. Using a 0.1% aqueous solution of TFA as solvent A, and a 90% aqueous solution of acetonitrile containing 0.1% TFA as solvent B, a sample was injected into the column, after which the ratio of A:B was held at 7:3 for first 3 minutes, and then changed to 6:4 by a linear concentration gradient for next 10 minutes. This concentration was maintained for 5 minutes. After changing the ratio of A:B to 7:3 for next one minute, this concentration was maintained for 5 minutes. The substrate THC was eluted at about 20.9 minutes under these conditions. A compound eluted at about 8.8 minutes was detected as a reaction product. This compound was aureusidin as described later.

Aureusidin was determined to be formed from THC by this reaction.

Example 4

Purification of Aurone Synthase

1) Enzyme Purification

Enzyme purification was carried out using as a starting material 32,175 g of snapdragon buds from which white petals were peering out from between calyx and flowers that had started to be colored yellow. 2400 ml of chilled buffer A (0.01 M sodium acetate, pH 5.0) and 120 g of polyvinylpolypyrrolidone (PVPP) were added per approximately 600 g of flowers and then crushed for 1 to 1.5 minutes with a whirling blender.

Extracts from the crushed flowers were centrifuged at 8000 rpm and 4° C. for 15 minutes, and ammonium sulfate was dissolved to 60% of saturation in the resulting supernatant. After stirring to dissolve, the solution was allowed to stand. The precipitate collected by centrifuging at 8000 rpm and 4° C. for 15 minutes was suspended in a minimum amount of buffer A and dialyzed against buffer A. The dialysate was centrifuged at 8000 rpm and 4° C. for 15 minutes, and the resulting supernatant was used as ammonium sulfate fraction concentrate. The ammonium sulfate fraction concentrate was stored frozen at −20° C. until SP-Sephadex C50 chromatography.

2) SP-Sephadex C50 Chromatography

The resulting ammonium sulfate fraction concentrate was subjected to the following procedure three times. The electrical conductivity of the ammonium sulfate fraction concentrate was measured after dialysis, and the concentrate was diluted with cold deionized water as necessary until the electrical conductivity became 0.8 to 1 mS at 4° C. The ammonium sulfate fraction concentrate was applied onto an SP-Sephadex C50 column (6 cm×25.5 cm; approx. 0.7 liters) which had been equilibrated thoroughly with buffer B (buffer A containing several μM THC). After the application, the column was thoroughly washed with buffer B. Elution was performed in 23 ml fractions while washing the column by applying a linear concentration gradient between buffer B (2.0 liters) and buffer B containing 0.6 M NaCl (2.0 liters). The active fractions (approx. 1200 ml) were collected, sterilized by filtration, and stored at 4° C. until ConA Sepharose chromatography.

3) ConA Sepharose Chromatography

ConA Sepharose chromatography was performed in twice for fraction A (containing 374,000 U in 1100 ml) and fraction B (containing 831,000 U in 2900 ml). $MnCl_2$ and $CaCl_2$ were dissolved in the fraction A to 1 mM each and applied onto a ConA Sepharose column (2 cm×12 cm; approx. 40 ml) which had been equilibrated with buffer C (buffer B containing 1 mM $MnCl_2$, 1 mM $CaCl_2$ and 0.5 M NaCl). After the application, the column was washed with approximately 0.3 liters of buffer C. The flow-through fraction and washing fraction (300 ml) contained 50,000 U each of activity respectively before application (13% each of the original activity).

After washing, elution was performed in 4 ml fractions while washing the column by applying a linear concentration gradient between buffer C (250 ml) and buffer C containing 0.2 M methyl-α-D-glucoside and 0.2 M methyl-α-D-mannopyranoside (250 ml) so as to collect active fractions (total 78 ml). The active fraction was thoroughly dialyzed against buffer D (5 mM potassium phosphate buffer (pH 5.0), 0.3 mM $CaCl_2$ and 3 to 6 μM THC). The washing fraction was combined with the remaining fraction B, and the second round of chromatography was carried out.

$MnCl_2$ and $CaCl_2$ were each dissolved to 1 mM in the remaining active fraction B, and applied onto a ConA Sepharose column (3.6 cm×12 cm; approx. 120 ml) which had been equilibrated with buffer C. After the application, the column was washed with approximately 0.3 liters of buffer C. The flow-through fraction and washing fraction (300 ml) contained little activity. After washing, elution was performed in 8 ml fractions while washing the column by applying a linear concentration gradient between buffer C (350 ml) and buffer C containing 0.2 M methyl-α-D-glucoside and 0.2 M methyl-α-D-mannopyranoside (350 ml) so as to collect active fractions (total 150 ml). After thoroughly dialyzing the active fraction against buffer D, the dialyzate was combined with the previous sample to obtain a active fraction (total 250 ml).

4) Gigapite Chromatography

Dialysate (250 ml) was applied onto a Gigapite column (Biochemical Industries, 2 cm×16 cm, 50 ml open column) which had been equilibrated with buffer D. After the application of the sample, the column was washed with buffer D (250 ml). Elution was performed in 4 ml fractions while washing the column by applying a linear concentration gradient between buffer D (200 ml) and 0.5 M potassium phosphate buffer (pH 5.0) (200 ml) so as to collect active fractions (total 120 ml).

5) HiLoad 16/60 Superdex 75 pg FPLC

{3-[(3-cholamidopropyl)dimethylammonio]-1-propanesulfonate} (CHAPS) was dissolved to a final concentration of 0.1% in the active fraction, followed by ultrafiltration using an Amicon PM10 film to concentrate to 18 ml. The following procedure was performed 6 times on the concentrated active fraction.

A chilled HiLoad 16/60 Superdex 75 pg column was equilibrated with buffer B containing 0.07% CHAPS and 0.15 M NaCl, eluted at a flow rate of 0.5 ml/min to obtain 2 ml fractions using an FPLC system. Active fractions were collected (total 63 ml).

6) SP-Sepharose FF FPLC

The resulting active fraction was thoroughly dialyzed at 4° C. against buffer E (buffer B containing 0.07% CHAPS). The following chromatography procedure was performed twice using an FPLC system. A chilled SP-Sepharose FF column (1×16 cm) was equilibrated with buffer E. After applying the sample onto the column, buffer E was used as solution A and buffer E containing 0.7 M NaCl was used as solution B. The column was washed for first 30 minutes with 95% solution A and 5% solution B, a linear concentration gradient to 55% solution A and 45% solution B was then applied for next 120 minutes, followed by elution for next 10 minutes under the same conditions. Elution was performed in 1.0 ml fractions at a flow rate of 0.5 ml/min. Active fractions (total 27.8 ml) were collected and stored at 4° C. after sterilizing by filtration.

7) Gigapite Column Chromatography 22 ml of the active fraction was further purified by Gigapite (1×14 cm) FPLC. 22 ml of sample was dialyzed overnight at 4° C. against 0.005 M potassium phosphate buffer (pH 5.0) containing 0.07% CHAPS, FPLC was performed under the following conditions, and the correlation between activity and protein band behavior was observed. FPLC was performed while chilling the column and buffer using 0.005 M potassium phosphate buffer (pH 5.0) containing 0.07% CHAPS and 0.3 mM $CaCl_2$ as solution A, and 0.5 M potassium phosphate buffer (pH 5.0) containing 0.07% CHAPS as solution B.

After washing the column for 30 minutes with 100% solution A at a flow rate of 0.5 ml/min, a linear concentration gradient to 95% solution A and 5% solution B was applied for next 6 seconds, and then to 20% solution A and 80% solution B for next 149 minutes 54 seconds, followed by eluting under the same conditions for next 155 minutes in 1.0 ml fractions.

Those fractions were collected that contained 40 kDa protein which demonstrated the best correlation with activity behavior based on chromatography and activity measurement results, and were used in primary structure analysis.

Example 5

Activity Measurement for Three Types Column Chromatography and SDS-PAGE

1) Superdex 200 Smart System

Fractionation was performed with a Superdex 200 Smart System using 50 μl of sample. The following procedure was performed at 4° C. using 0.01 M sodium acetate (pH 5.0) containing 0.07% CHAPS and 0.15 M NaCl as a solvent. Gel filtration chromatography was performed by fractioning in 40.0 μl aliquots at a flow rate of 40.0 μl/min. Activity measurement and SDS-PAGE was performed for the sample. Enzyme activity was eluted in the vicinity of a molecular weight of 43 kDa, and among those proteins contained in the sample, the behavior of the 40 kDa protein correlated most closely with activity behavior.

2) Alkyl-Sepharose HR5/5 FPLC

250 µl of sample was dialyzed overnight at 4° C. against 0.01 M sodium acetate (pH 5.0), and ammonium sulfate was dissolved to a final concentration of 2 M. Alkyl-Sepharose HR5/5 FPLC was performed at room temperature. Using 0.01 M sodium acetate (pH 5.0) containing 2 M $(NH_4)_2SO_4$ as solution A, and 0.01 M sodium acetate (pH 5.0) as solution B, the column was washed with 100% solution A for first 10 minutes, a linear concentration gradient to 100% solution B was applied for next 50 minutes, and elution was performed for next 5 minutes under the same condition in 0.5 ml fractions.

400 µl of each fraction was concentrated to 40 µl with Ultra-Free C3GC (molecular weight fractionated: 10,000, Millipore), and 10 µl of the concentrate was analyzed by SDS-PAGE and measured activity. Among the proteins contained in the sample, the best correlation was observed between activity behavior and the behavior of the 40 kDa protein.

3) Gigapite HR5/5 FPLC

300 µl of sample was dialyzed overnight at 4° C. against 0.005 M potassium phosphate buffer (pH 5.0) containing 0.07% CHAPS. Gigapite HR5/5 FLPC was performed at room temperature under the following conditions.

Using 0.005 M potassium phosphate buffer (pH 5.0) containing 0.07% CHAPS and 0.3 mM $CaCl_2$ as solution A, and 0.5 M potassium phosphate buffer (pH 5.0) containing 0.07% CHAPS as solution B, the column was washed with 100% solution A for first 5 minutes, and a linear concentration gradient to 80% solution A and 20% solution B was applied for next 6 seconds and then to 20% solution A and 80% solution B for next 44 minutes 54 seconds, after which 0.5 ml fractions were eluted. Activity measurement and SDS-PAGE electrophoresis were then performed. Among the proteins contained in the sample, the best correlation was observed between the behavior of the 40 kDa protein and activity behavior.

As a result of conducting column chromatography with the Superdex 200 Smart System, Alkyl-Sepharose FPLC and Gigapite FPLC, a close correlation was demonstrated between the behavior of the approximately 40 kDa protein band and activity behavior.

Example 6

Characteristics of Aurone Synthase

It was confirmed that purified aurone synthase converts both THC and pentahydroxychalcone to aureusidin. The resulting product was confirmed to be aureusidin by HPLC analysis.

The molecular weight of this enzyme was determined to be 40 kDa with SDS polyaklylamide gel electrophoresis, and 43 kDa with gel electrophoresis using Superdex 200. This data revealed that aurone synthase is a monomer. Enzyme activity was inhibited by 90% or more in the presence of 1 mM monovalent copper ion, bivalent copper ion, bivalent iron ion and trivalent iron ion. In addition, binding to ConA Sepharose suggested the possibility that the enzyme contains sugar. In addition, activity increased somewhat when hydrogen peroxide was added.

A product expected to be aureusidin was formed when the enzyme reacted with THC as substrate, and its structure was determined by collecting a large amount of this product. 20 ml of 1 M sodium acetate buffer (pH 5.0) containing 10 mM hydrogen peroxide, 20 ml of enzyme solution, 58 ml of water and 10 mg (0.5 ml) of THC were mixed and held for 3.5 hours at 30° C. After reacting, the reaction mixture was adsorbed onto Sep-Pak C18 and eluted with methanol. After concentrating with an evaporator, it was purified with separation HPLC, using a YMC D-0DS-5 S-5 120A (2.5×25 cm) column. Elution was performed at a flow rate of 4.5 ml/min using an aqueous solution of 40% acetonitrile containing 0.03% TFA. The peak that eluted at approximately 17 minutes was collected and dried to obtain approximately 4.9 mg of product. Determination of the structure of the compound by $^1$H-NMR and mass spectrometry revealed it to be aureusidin.

Example 7

Determination of Amino Acid Sequences of Aurone Synthase

Approximately 1 nmol of the resulting aurone synthase, to which SDS had been added to a final concentration of 2%, was subjected to a preparative electrophoresis (Biophoresis, Atoh) under non-reducing conditions so as to recover a polypeptide having a molecular weight of 41,000. When this polypeptide was separated with reverse-phase HPLC using a C4 column (Develosil 300C4-HG-5), a single peak was detected, confirming that the recovered aurone synthase is pure.

This polypeptide was digested by lysylendopeptidase AP1. The buffer for the reaction was 40 mM Tris-HCl (pH 9.5) containing 0.01% Tween 20 and 2 M urea. The digestion product was purified with reverse-phase HPLC using a Bakerbond ODS (4.6 mm×25 cm) column. Namely, an aqueous solution of 0.05% trifluoroacetic acid was used as solution A, and 80% acetonitrile containing 0.05% trifluoroacetic acid was used as solution B, and a linear concentration gradient to 90% solution A and 10% solution B was applied for first 5 minutes, and then to 100% solution B for next 80 minutes to separate the peptides.

The sequences of the purified peptides were determined with a peptide sequencer using a vapor phase method. The determined sequences are shown below.

P5: (K)KLGYVYQDVEIP (SEQ ID No. 3)
P8: (K)IVYRQMVSSAK (SEQ ID No. 4)
P11: (K)TPQLFFGRPYRRGDQEF (SEQ ID No. 5)
P4–5: (K)IIDFELPXPSTTMRVRRAAHLVDDAYIXK (SEQ ID No. 6)

Example 8

Construction of cDNA Library of Snapdragon Petals

A cDNA library from snapdragon petals was constructed according to the method described below. RNA was obtained from 5 g of fresh petals collected immediately before blooming from yellow snapdragons by using guanidine thiocyanate/cesium chloride as described in detail in Methods in Molecular Biology, Vol. 2 (Humana Press Inc., 1984) of R. McGookin, et al., followed by purification of PolyA+RNA using Oligodex dT30 (Roche Japan). A cDNA library was then prepared with this PolyA+RNA and λZAPII (Stratagene) as a vector, by using a cDNA synthesis kit and Uni-XR vector kit (Stratagene), as recommended by Stratagene. The resulting library was composed of 1.6×10$^5$ plague-forming units (pfu).

Example 9

Acquisition of Gene Expressed in Yellow Snapdragons by Subtraction

Subtraction is one of a method for acquiring a gene specifically expressed in a certain tissue at a certain time, and here was carried out using the PCR-Select™ cDNA Subtraction Kit (Clontech) as recommended. cDNA derived from yellow snapdragon petals was used as a tester, while mRNA derived from pink snapdragon petals was used as a driver. DNA fragments ultimately amplified by PCR were subcloned to PCRII™ vector using a TA cloning kit (Invitrogen), followed by determination of their respective nucleotide sequences.

Among these, the amino acid sequence expected to be encoded by a gene named SYP8 is shown in Sequence ID No. 7.

RQMVSSAKTPQLFFGRPYRRGDQEFPGVGSIEL-
VPHGMIHLWTGSENTPYGENMGAFY STARD-
PIFFAHHSNVDRMWSIWKTLGGPRRT-
DLTDPDFLDASFVFCDENAEMVRVKVRDC
LDGKKLG (SEQ ID No. 7)

Within this amino acid sequence, the sequence consisting of 25 amino acids from the N-terminal and the sequence consisting of 4 amino acids from the C-terminal coincided with sequences P5, P8 and P11 obtained in Example 7. Namely, this gene fragment was found to encode aurone synthase.

Example 10

Acquisition of Full-Length Aurone Synthase Gene

The previously described snapdragon cDNA library was screened by using the DNA fragment SYP8. Screening of the library was performed by using a non-radioactive system DNA detection kit (Boehringer). As a result of screening approximately 200,000 plaques, a large number of positive signals were obtained. 20 of these plaques were randomly selected, pure plaques were isolated by secondary screening, and the nucleotide sequence of the longest clone among these, SYP8–17, was determined.

The nucleotide sequence was determined with a synthesized oligonucleotide primer by using a DNA Sequencer Model-373A (ABI). This nucleotide sequence and its deduced amino acid sequence are shown in SEQ ID No. 1. When a database search was performed for this amino acid sequence, this gene demonstrated low homology with polyphenoloxidase gene (GenBank Association No. L29451, D45385, Z11702), and it was found to be a novel gene. Furthermore, the main region having homology with polyphenoloxidase was a copper-binding region which is the active center of polyphenoloxidase.

Example 11

Expression Manner of Aurone Synthase Gene

Figures 3, 4:
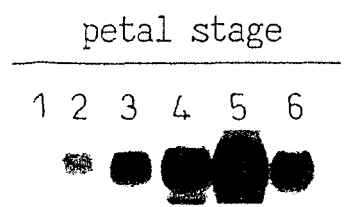
FIG. 3 shows the results of Northern analysis in each organ of yellow snapdragon using SYP8-17.
FIG. 4 shows the results of Northern analysis at each stage of development of the petals of yellow snapdragon using SYP8-17.
Figure 5:
FIG. 5 shows the results of Northern analysis in yellow, pink and white snapdragon petals using SYP8-17.

Organs and petals of yellow snapdragon at each stage of developments were used for Northern analysis by using SYP8-17 as a probe. In addition, Northern analysis was also performed by using the petals of yellow, pink and white snapdragons. The method was according to Molecular Cloning (Sambrook, et al., Cold Spring Harbour Laboratory Press, 1989). The results are shown in FIGS. 3, 4 and 5. Aurone synthase gene was specially expressed in petals, and moreover the expression in petals occurs parallel to biosynthesis of aurones. In addition, in the pink and white petals of snapdragons in which the accumulation of mRNA of aurone synthase gene was either low or not observed at all, aurone synthesis activity was extremely weak or not detected as compared with that in the yellow petals of snapdragons. These results suggest that the resulting gene is involved in aurone synthesis.

Example 12

Preparation of Verbena cDNA Library mRNA was purified in the manner previously described from 5 g of fresh flower buds of Verbena variety Hanatemari Violet (Suntory), followed by preparation of a cDNA library, as described in Example 8. A resulting library was composed of $0.8 \times 10^6$ plaque-forming units (pfu).

Example 13

Cloning of Verbena Chalcone Isomerase cDNA

The following primers were synthesized based on the amino acid sequences, Phe-Val/Ile-Lys-Phe-Thr-Ala-Ile (SEQ ID NO. 8), Lys-Trp-Lys-Gly-Lys-Thr/Pro (SEQ ID NO. 9) and a reverse sequence of a amino acid sequence, His-Ala-Val-Cys-Asn-Glu (SEQ ID NO. 10), these amino acid sequences are well conserved sequences compared with the known amino acid sequences of chalcone isomerase derived from higher plants.

CHI-F1: 5'-TT(T,C) (A,G)TN AA(A,G) TT(T,C) ACN GCN AT-3' (SEQ ID NO. 11)
CHI-F2: 5'-AA(A,G) TGG AA(A,G) GGN AA(A,G) (A,C)C-3' (SEQ ID NO. 12)
CHI-R2: 5'-(A,G)TG NGC NAC (A,G)CA(A,G)TT (T,C) TC-3' (SEQ ID NO. 13)

Using a combination of primers of previously synthesized CHI-F1 and CHI-R2, or CHI-F2 and CHI-R2, after reacting for 2 minutes at 96° C., the reaction was repeated 30 times for 1 minute at 96° C., 1.5 minutes at 42° C. and 3 minutes at 72° C., and finally reacted for 7 minutes at 72° C. When PCR was performed again under the same conditions using the resulting PCR product as a template, an approximately 200 bp PCR product was amplified for the combination of CHI-F1 and CHI-R2 primers, while approximately 800, 600, 400 and 150 bp PCR products were amplified with the combination of CHI-F2 and CHI-R2 primers.

The resulting PCR products were subcloned to PCRII™ vector using a TA cloning kit (Invitrogen). The nucleotide sequences of the subcloned DNA fragments were determined by using the DNA Sequencer Model 373A (ABI). The PCR products obtained with each combination of primers CHI-F1 and CHI-R2, or primers CHI-F2 and CHI-R2, each had a common sequence with different lengths of 222 bp and 159 bp. The deduced amino acid sequences of these products exhibited a high degree of homology with chalcone isomerase derived from other higher plants.

PCR was performed by using CHI-F1 and CHI-R2 primers and an approximately 230 bp fragment obtained by digesting PCRII™ vector containing 222 bp Hanatemari chalcone isomerase as a template. After reacting for 2 minutes at 95° C. by PCR using the amplified PCR product of approximately 230 bp as a template, the reaction was repeated 25 times for 1 minute at 95° C., for 1 minute at 42° C. and for 4 minutes at 72° C., and finally reacting for 7 minutes at 72° C., after which it was labeled with digoxigenin and used as a probe for screening. Screening from the Hanatemari cDNA library was carried out by the recommended method with a non-radioactive system DNA detection kit (Boehringer).

The chalcone isomerase genes of other plants can also be obtained by using a similar method.

Example 14

Preparation of SYP8 Antiqen

SYP8 gene described in Example 9 was expressed in *E. coli* using the QIA Expressionist Kit (QIAGEN) and an expression product was purified. Since the molecular weight of the purified preparation of aurone synthase is 40 to 43 kDa, the peptides of the N-terminal and C-terminal were predicted to be truncated in the mature protein.

Therefore, QESYP8-5' and QESYP8-31 primers were synthesized so as to express the region from the 61st glycine residue to the 416th lysine residue of the amino acid sequence shown in SEQ ID NO. 2.

QESPY8-5': 5'-AA GAA TCC GGC CCT ATC GCC-3' (SEQ ID NO. 14)

QESPY8-3': 5'-GGG TTC GAA GAA TTC ATC TCT G-3' (SEQ ID NO. 15)

A BamHI site was introduced into the QESYP8-5' primer, and a HindIII site was introduced into the QESYP8-3' primer. A PCR reaction was carried out using a reaction mixture of a total of 100 μl comprising 30 pmol each of the synthesized QESYP8-5' and QESYP8-3' primers, 1 ng of SYP8-17 gene, 1× cloned pfu DNA polymerase buffer (Stratagene), 200 μM dNTPs and 5 units of cloned pfu DNA polymerase (Stratagene). After holding at 94° C. for 45 seconds, the reaction was carried out for 25 cycles consisting of 45 seconds at 94° C., 45 seconds at 50° C. and 4 minutes at 72° C., after which the reaction was finally held at 72° C. for 10 minutes. The resulting PCR product was subcloned to pCR2.1 TOPO™ vector by using a TA cloning kit (Invitrogen) to obtain plasmid pCR.QESYP8. pCR.QESYP8 was treated with BamHI and HindIII, and a resulting DNA fragment of approximately 1 kb was ligated to a pQE30 vector (QIAGEN) which had been similarly treated with BamHI and HindIII so as to construct plasmid pQESYP8. pQESYP8 was transformed into *E. coli* M15 [pRep4]. Expression of SYP8 protein in *E. coli* and its purification were performed according to the method recommended by the manufacturers. Since the resulting purified protein was observed to have a small amount of impurity protein according to SDS-PAGE analysis, it was further purified as described below. Protein solution was concentrated to approximately 1 ml using Centriprep 10 (Amicon), dialyzed with water and freeze-dried. After treating with SDS, the impurity protein was separated using Biophoresis (Atoh, 4.5% concentration gel, 10% separation gel, 15 mA, 0.8 ml fractions). Simultaneously with concentration using Ultra-Free 10 (Millipore), the final purified preparation was transferred to PBS buffer (prepared by dissolving 8 g of NaCl, 0.2 g of KCl, 1.44 g of $Na_2HPO_4$ and 0.24 g of $KH_2PO_4$ in 1 liter and adjusting the pH to 7.4 with hydrochloric acid) containing 0.1% CHAPS. The protein concentration in the finally purified preparation was 1.0 mg/ml.

Example 15

Preparation of SYP8 Antibody Column

Two rabbits were immunized four times with 0.2 mg each of SYP8 antigen (1.0 mg/ml) prepared in Example 14. The initial immunization was performed using Freund's complete adjuvant. Additional immunizations were performed using Freund's incomplete adjuvant. The additional immunizations were performed on days 14, 42 and 56 after the initial immunization. The method was in accordance with Vol. 12 of the Shin Seikagaku Jikken Koza. Blood samples were collected on days 52, 66 and 70 after the initial immunization, and after holding the resulting blood for 30 minutes at 37° C., it was allowed to stand undisturbed overnight at 4° C. The clot was removed to obtain antiserum. After diluting the antiserum two-fold with 0.85% NaCl, one half volume of chilled Freegen (Hoechst Japan) was added and after stirring vigorously, the mixture was centrifuged for 5 minutes at 1500 rpm to remove fat, after which the resulting supernatant was used as antiserum.

The defatted anti-SYP8 antiserum (approx. 45 ml) was diluted with an equal volume of 0.15 M NaCl solution, followed by the addition of ammonium sulfate to 33% saturation and centrifuging for 30 minutes at 8000 rpm. The precipitate was dialyzed with buffer A (0.05M Tris-HCl, pH 8.6, 0.15 M NaCl). The dialysate was applied to a Hi Trap Protein A column (1 ml) to purify an IgG fraction. Namely, the dialyzed sample was applied onto the Hi Trap Protein A column equilibrated with buffer A, and after washing the column with buffer A, the dialyzed sample was sequentially eluted using buffer B (0.05 M citrate buffer, pH 5.3, 0.15 M NaCl), buffer C (0.05 M acetate buffer, pH 4.3, 0.15 M NaCl) and buffer D (0.05 M glysine buffer, pH 2.3, 0.15 M NaCl). IgG was confirmed to be present in both the buffer C and buffer D fractions according to ultraviolet absorption and immunodot blotting, and these fractions were mixed to form an IgG fraction. The amount of protein of the fraction was approximately 70 mg. The resulting IgG fraction was dialyzed with 0.1 M $NaHCO_3$ and 0.5 M NaCl, after which it was concentrated to approximately 2 mg/ml with Centricon 10 (Amicon). 4.5 g of CNBr-activated Sepharose 4B was suspended in 45 ml of 1 mM HCl and washed with 500 ml of 1 mM HCl over a Buchner funnel. The washed resin was added a little at a time to the concentrated IgG solution and suspended, and shaken overnight at 4° C. to immobilize the IgG. The resin was collected by filtration with aspiration over a Buchner funnel, resuspended in 30 ml of 0.2 M Tris-HCl buffer (pH 8.5), and the suspension was shaken for two nights at 4° C. so as to inactivate residual active groups on the resin. Next, the resin was sequentially washed with 0.2 M acetate buffer (pH 5.0), Tris-HCl buffer (pH 8.5), 0.01 M potassium phosphate buffer (pH 7.8) and 0.2 M NaCl. As a control, anti-band A IgG and anti-β-galactosidase IgG were respectively immobilized to Sepharose 4B in the same manner. This Sepharose 4B was used as IgG-Sepharose 4B suspension (anti-SYP8, anti-band A, anti-β-galactosidase) in Example 16. Furthermore, the weight of reacted IgG per unit resin weight was set to be roughly the same for all three types. The immobilization yield was 90 to 100%.

Example 16

Immunoprecipitation Experiment 0, 200, 500 and 815 μl each of aqueous bovine serum albumin solution (final concentration 0.1%) and IgG- Sepharose 4B suspension prepared in Example 15 (anti-SYP 8, anti-band A, anti-β-galactosidase; resin phase:liquid phase=2:1 v/v) were added to a amount of enzyme solution, and then the mixture was brought to a final volume of 1 ml with 0.01 M potassium phosphate buffer (pH 7.8) and 0.2 M NaCl. After shaking the mixture for 24 hours at 4° C. and centrifuging for 20 minutes at 13,000 rpm, aurone synthase activity of the supernatant was measured.

Namely, aurone synthase activity was measured by adding CHAPS having a final concentration of 0.1%, 5 mM $H_2O_2$ and 0.1 M citrate buffer to the supernatant to make the pH 5.4, bringing the total volume to 395 μl and holding for 15 minutes at 30° C., followed by addition of 5 μl of THC (dissolved with ethanol so that A366=600) to start the reaction. After allowing to react for 60 minutes at 30° C., 100 μl of 10% TFA and 90% acetonitrile were added to stop the reaction. Activity was then measured by analyzing the reaction mixture by HPLC as described in Example 3.

Figure 6:
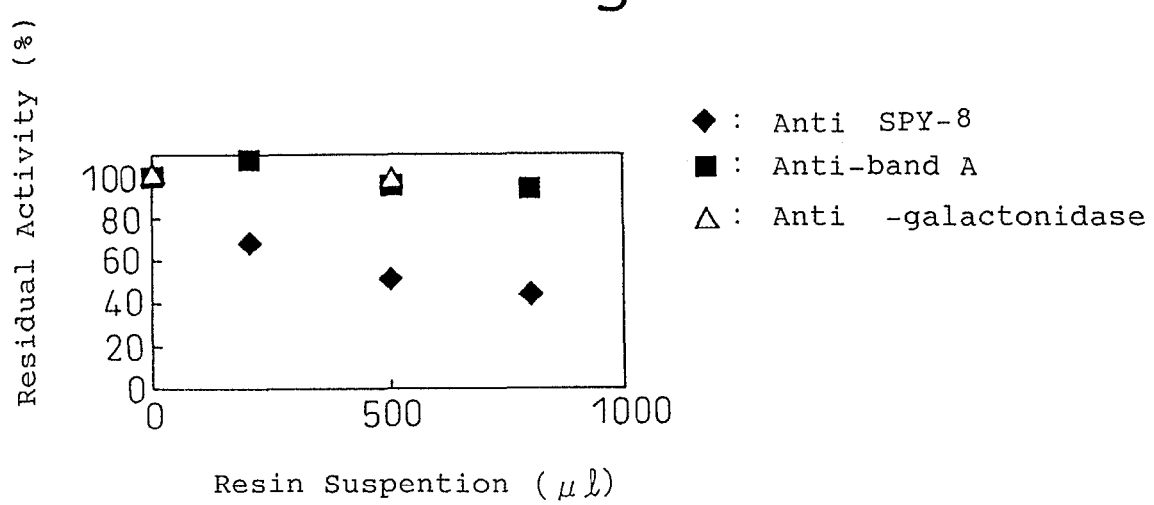
FIG. 6 is a graph showing an inhibition mode of aurone synthase activity by adding antibody against aurone synthase SYP-8 (anti-SYP-8) and other reference antibodies (anti-band A and anti-β-galactosidase).

As shown in FIG. 6, when anti-SYP8-IgG-Sepharose 4B was used, enzyme activity in the supernatant decreased dependent on the amount of anti-SYP8-IgG-Sepharose 4B added. There was no change in aurone synthase activity in the case of adding anti-band A-IgG-Sepharose 4B or anti-β-galactosidase-IgG-Sepharose 4B as a control. In addition, the resin collected as precipitate was washed with 0.01 M potassium phosphate buffer and 0.2 M NaCl, followed by measurement of aurone synthase activity. As a result, aurone synthase activity was observed only for anti-SYP8-IgG-Sepharose 4B.

Figure 7:
FIG. 7 shows SYP8 protein remaining in supernatant after addition of anti-SYP8-IgG-Sepharose 4B.

When the supernatant was analyzed by SDS-PAGE and Western blotting, the signal of aurone synthase decreased dependent on the amount of anti-SYP8-IgG-Sepharose 4B as shown in FIG. 7. On the other hand, in a similar experiment using anti-band A-IgG-Sepharose 4B as control, the signal of the aurone synthase gene was constant regardless of the amount of anti-band A-IgG-Sepharose 4B added.

According to these results, SYP8 gene was confirmed to encode aurone synthase. Note that an approximately 80 kDa signal was detected dependent on the amount of anti-SYP 8-IgG-Sepharose 4B added in FIG. 7. Since this signal increases with storage time of the resin until the experiment, this signal is thought to have been derived from IgG liberated from the Sepharose 4B resin.

Example 17

As was described in Example 10, aurone synthase demonstrates weak homology with polyphenol oxidase at the amino acid level, and the major region possessing that homology is the region that binds to copper. Accordingly, since it is expected that aurone synthase is also a copper enzyme, atomic absorption analysis was performed on aureusidin synthase. The Shimazu AA-6700F was used for the measurement system, and measurement was performed in the furnace measurement mode at a wavelength of 324.8 nm.

A calibration curve (calibration range: 0 to 9 ppb) was prepared using a 1000 ppm copper standard solution (Wako Pure Chemical Industries) diluted 1000-fold with concentrated sulfuric acid. Since other organic substances present may obstruct measurement in the case of analysis by atomic absorption analysis, measurement of the atomic absorption of copper was confirmed to be possible even in acetic acid buffer containing 0.1% CHAPS in advance by using mushroom tyrosinase (enzyme containing copper ion) prior to measurement. Next, pure aureusidin synthase (200 μl) was thoroughly dialyzed against acetic acid buffer (pH 6.0) containing 0.1% CHAPS. Known amounts of several standard proteins were analyzed by SDS-PAGE, the darkness of the resulting silver-colored bands was quantified with an image scanner, and a calibration curve was prepared for determining the amount of protein from band darkness. A portion of the pure aureusidin synthase was applied to SDS-PAGE under the same conditions, its silver-colored band was quantified with an image scanner, and protein concentration was calculated from the previously prepared calibration curve. Copper was detected by adding 0.5 μl of concentrated sulfuric acid (1.38 N) to 100 μl of pure aureusidin synthase and measuring. Accordingly, this enzyme was clearly shown to be a copper enzyme.

Example 18

Aurone Synthesis Activity of Tyrosinase

After mixing tyrosinase (Sigma catalog no. T7755; 0.04 mg/ml, 10 μl), 0.1 M sodium phosphate buffer (pH 6.5, 335 μl), 9% CHAPS (20 μl) and milli-Q water (20 μl), the mixture was incubated for 10 minutes at 30° C., followed by the addition of tetrahydroxychalcone (THC, 4.3 mM in ethanol, 15 μl), stirring immediately and reacting for 30 minutes at 30° C. After reaction, 100 μl of reaction stopping solution (10% trifluoroacetate solution containing 90% acetonitrile) was added to the reaction mixture to stop the reaction, followed by HPLC analysis. Analysis was performed in the same manner as described in Example 3. Water was used instead of tyrosinase as a control.

In the case of addition of tyrosinase, the substrate THC was eluted in approximately 15.9 minutes, while the reaction product aureusidin was eluted in approximately 12.5 minutes. On the other hand, in the case of addition of water instead of tyrosinase, the substrate THC was eluted in approximately 16 minutes, while aureusidin was not eluted.

In addition, the reaction was carried out under the same conditions using pentahydroxychalcone (PHC) instead of THC as a substrate, and using 0.116 M sodium citrate phosphate buffer (pH 5.4) as a buffer. Similarly, water was used instead of tyrosinase as a control.

In the case of addition of tyrosinase, the substrate PHC was eluted in approximately 14.7 minutes, while the reaction product aureusidin was eluted in approximately 12.5 minutes. On the other hand, in the case of adding water instead of tyrosinase, although the substrate PHC was eluted in approximately 14.6 minutes, aureusidin was not eluted.

Thus, tyrosinase was clearly shown to also have activity to synthesize aurone.

INDUSTRIAL APPLICABILITY

As has been described above, according to the present invention, a reaction in which aureusidin, a kind of aurone, is synthesized from tetrahydroxychalcone was observed for the first time, aureusidin synthase that catalyzes this reaction was isolated and purified, its amino acid sequence was determined, and its gene was cloned. Here, although snapdragon was used for the enzyme source, enzymes that synthesize aurones can be purified from other plants containing aurones using a similar method, and their genes can be obtained.

Alternatively, since genes encoding enzymes that catalyze the same reaction are known to have mutually homologous nucleotide sequences and hybridize, a gene encoding an enzyme that synthesizes aurones can be obtained from another source based on the cDNA obtained from snapdragon.

In addition, a gene that encodes protein having activity to synthesize aurones by using chalcones as substrates can also be obtained from polyphenol oxidase.

The introduction of a target gene into a plant is currently widely known, and the present invention makes it possible to breed yellow flowers from plant species that do not inherently possess yellow flowers. Moreover, it is also possible to change the color tone in plant species having yellow flowers.

What is claimed is:

1. An isolated nucleic acid encoding an amino acid sequence as shown in SEQ ID NO: 2.

2. A vector comprising a nucleic acid as set forth in claim 1.

3. An isolated host cell transformed with a vector as set forth in claim 2.

4. An isolated host cell according to claim 3, wherein said host cell is a microorganism, an animal cell or a plant cell.

5. An isolated nucleic acid sequence having the nucleotide sequence of SEQ ID NO:1.

6. A vector comprising a nucleic acid as set forth in claim 5.

7. An isolated host cell transformed with a vector as set forth in claim 6.

8. An isolated host cell according to claim 7, wherein said host cell is a microorganism, an animal cell or a plant cell.

* * * * *

SEQUENCE LISTING

<160> NUMBER OF SEQ ID NOS: 15

<210> SEQ ID NO 1
<211> LENGTH: 1951
<212> TYPE: DNA
<213> ORGANISM: Antirrhinum majus
<220> FEATURE:
<221> NAME/KEY: CDS
<222> LOCATION: (96)..(1781)

<400> SEQUENCE: 1

```
aaattacatt gcttcctttg tcccaccttc caccaccaat atatacaact tcctcagcta        60
gttgtttatt atcaatcaaa taaaattatt tccca atg ttc aaa aat cct aat         113
                                      Met Phe Lys Asn Pro Asn
                                      1               5 atc cgc tat cac aaa cta tct tcc aaa tcc aat gac aac gat caa gaa         161
Ile Arg Tyr His Lys Leu Ser Ser Lys Ser Asn Asp Asn Asp Gln Glu
             10                  15                  20 tcc tcc cat cgt tgt aag cac att cta tta ttt ata ata acc tta ttc         209
Ser Ser His Arg Cys Lys His Ile Leu Leu Phe Ile Ile Thr Leu Phe
         25                  30                  35 cta ctt ata gtt ggc ctg tac atc gcc aac tct ctc gcc tat gcc cgg         257
Leu Leu Ile Val Gly Leu Tyr Ile Ala Asn Ser Leu Ala Tyr Ala Arg
     40                  45                  50 ttt gcc tcg acc tca acc ggc cct atc gcc gcc cct gat gtc acc aaa         305
Phe Ala Ser Thr Ser Thr Gly Pro Ile Ala Ala Pro Asp Val Thr Lys
55                  60                  65                  70 tgt ggt cag cca gac ttg cca cct ggc aca gcc cca ata aac tgt tgt         353
Cys Gly Gln Pro Asp Leu Pro Pro Gly Thr Ala Pro Ile Asn Cys Cys
                 75                  80                  85 ccc cca atc ccc gct aaa atc atc gat ttc gag cta cca cct ccc tcc         401
Pro Pro Ile Pro Ala Lys Ile Ile Asp Phe Glu Leu Pro Pro Pro Ser
             90                  95                 100 act acc atg agg gtt cgc cgt gcg gct cat tta gtt gat gat gca tac         449
Thr Thr Met Arg Val Arg Arg Ala Ala His Leu Val Asp Asp Ala Tyr
        105                 110                 115 att gcc aaa ttc aag aaa gcc gtt gag ctt atg cga gct cta cct gag         497
Ile Ala Lys Phe Lys Lys Ala Val Glu Leu Met Arg Ala Leu Pro Glu
    120                 125                 130 gat gac cct cgt agc ttc aag caa caa gct aac gtc cat tgc gct tac         545
Asp Asp Pro Arg Ser Phe Lys Gln Gln Ala Asn Val His Cys Ala Tyr
135                 140                 145                 150 tgc gcg ggg gcg tat aat caa gcc ggt ttc aca aac cta aag ctc caa         593
Cys Ala Gly Ala Tyr Asn Gln Ala Gly Phe Thr Asn Leu Lys Leu Gln
                155                 160                 165 atc cac cga tct tgg ctt ttt ttc ccg ttc cat aga tat tat atc tac         641
Ile His Arg Ser Trp Leu Phe Phe Pro Phe His Arg Tyr Tyr Ile Tyr
            170                 175                 180 ttt ttt gaa aga ata ttg gga aaa cta atc aat gat aca act ttt gct         689
Phe Phe Glu Arg Ile Leu Gly Lys Leu Ile Asn Asp Thr Thr Phe Ala
        185                 190                 195 ctc caa ttt tgg aac tat gat tca cct ggt gga atg aca atc cca tca         737
```

```
      Leu Gln Phe Trp Asn Tyr Asp Ser Pro Gly Gly Met Thr Ile Pro Ser
          200                 205                 210 atg ttt att gat act aat tct tcg ctg tac gat agt tta cgg gac agt        785
Met Phe Ile Asp Thr Asn Ser Ser Leu Tyr Asp Ser Leu Arg Asp Ser
215                 220                 225                 230 aat cat cag cca cca acc atc gta gac ttg aac tac gcc ttt tct gat        833
Asn His Gln Pro Pro Thr Ile Val Asp Leu Asn Tyr Ala Phe Ser Asp
                235                 240                 245 tcc gac aat acc act act cct gaa gag caa atg att ata aac ctt aaa        881
Ser Asp Asn Thr Thr Thr Pro Glu Glu Gln Met Ile Ile Asn Leu Lys
            250                 255                 260 att gtg tac aga caa atg gtg tcg agc gct aag act cca cag ctt ttc        929
Ile Val Tyr Arg Gln Met Val Ser Ser Ala Lys Thr Pro Gln Leu Phe
        265                 270                 275 ttc ggc cgc cca tac cga cgt ggg gac caa gag ttt ccc ggg gtg ggg        977
Phe Gly Arg Pro Tyr Arg Arg Gly Asp Gln Glu Phe Pro Gly Val Gly
    280                 285                 290 tcg att gag tta gtc cct cat ggc atg ata cat tta tgg acc ggt tct       1025
Ser Ile Glu Leu Val Pro His Gly Met Ile His Leu Trp Thr Gly Ser
295                 300                 305                 310 gag aac acg ccc tat ggc gag aac atg ggg gct ttc tac tca acg gct       1073
Glu Asn Thr Pro Tyr Gly Glu Asn Met Gly Ala Phe Tyr Ser Thr Ala
                315                 320                 325 aga gac ccg ata ttt ttt gct cat cat tcg aac gtc gat aga atg tgg       1121
Arg Asp Pro Ile Phe Phe Ala His His Ser Asn Val Asp Arg Met Trp
            330                 335                 340 tcc ata tgg aag acc cta gga ggg ccg cgg agg acg gac tta aca gat       1169
Ser Ile Trp Lys Thr Leu Gly Gly Pro Arg Arg Thr Asp Leu Thr Asp
        345                 350                 355 cca gat ttt ctt gat gcg tct ttc gtt ttt tat gac gaa aac gca gag       1217
Pro Asp Phe Leu Asp Ala Ser Phe Val Phe Tyr Asp Glu Asn Ala Glu
    360                 365                 370 atg gtt cgg gtc aag gtt cgg gat tgc tta gat gaa aag aaa cta ggg       1265
Met Val Arg Val Lys Val Arg Asp Cys Leu Asp Glu Lys Lys Leu Gly
375                 380                 385                 390 tac gtt tat caa gat gtg gag att ccg tgg ctc aac act cgt cca aca       1313
Tyr Val Tyr Gln Asp Val Glu Ile Pro Trp Leu Asn Thr Arg Pro Thr
                395                 400                 405 cca aaa gtt tct ccg tct cta ctt aag aaa ttt cat aga aca aac act       1361
Pro Lys Val Ser Pro Ser Leu Leu Lys Lys Phe His Arg Thr Asn Thr
            410                 415                 420 gcc aat ccg aga caa gtt ttt cct gcg ata ctt gac aga gtc tta aaa       1409
Ala Asn Pro Arg Gln Val Phe Pro Ala Ile Leu Asp Arg Val Leu Lys
        425                 430                 435 gtt atc gtg acg agg ccg aag aaa act aga agt agg aaa gaa aag gac       1457
Val Ile Val Thr Arg Pro Lys Lys Thr Arg Ser Arg Lys Glu Lys Asp
    440                 445                 450 gag tta gaa gag att tta gtg att gaa ggg att gaa ctg gaa aga gac       1505
Glu Leu Glu Glu Ile Leu Val Ile Glu Gly Ile Glu Leu Glu Arg Asp
455                 460                 465                 470 cac ggg cac gta aaa ttc gac gtt tat att aat gct gac gaa gat gac       1553
His Gly His Val Lys Phe Asp Val Tyr Ile Asn Ala Asp Glu Asp Asp
                475                 480                 485 ctt gcg gtg att tcg ccg gag aat gct gag ttc gcc ggg agt ttc gtg       1601
Leu Ala Val Ile Ser Pro Glu Asn Ala Glu Phe Ala Gly Ser Phe Val
            490                 495                 500 agt ctg tgg cac aaa cct ata aag ggg aag agg aca aag acg cag tta       1649
Ser Leu Trp His Lys Pro Ile Lys Gly Lys Arg Thr Lys Thr Gln Leu
        505                 510                 515
```

-continued

```
tta aca ttg tcg att tgt gat att ttg gag gat ttg gat gct gac gaa   1697
Leu Thr Leu Ser Ile Cys Asp Ile Leu Glu Asp Leu Asp Ala Asp Glu
    520                 525                 530 gat gat tat gtg ttg gtc act ttg gtt ccg aga aac gcc gga gat gcg   1745
Asp Asp Tyr Val Leu Val Thr Leu Val Pro Arg Asn Ala Gly Asp Ala
535                 540                 545                 550 atc aag att cat aat gtc aag att gag ctt gat ggc taataaattc        1791
Ile Lys Ile His Asn Val Lys Ile Glu Leu Asp Gly
                555                 560 tattgatttc ttctcaacct acagttgatc atttaccgat tgattattcc aataaaagta  1851
tctcatgtac caatatcgat cgtattaatc gtaatacttt cagattttta tttatttaaa  1911
agcagttgta taaatggtga aataaggatt acttttgag                         1951
```

<210> SEQ ID NO 2
<211> LENGTH: 562
<212> TYPE: PRT
<213> ORGANISM: Antirrhinum majus

<400> SEQUENCE: 2

```
Met Phe Lys Asn Pro Asn Ile Arg Tyr His Lys Leu Ser Ser Lys Ser
1               5                   10                  15

Asn Asp Asn Asp Gln Glu Ser Ser His Arg Cys Lys His Ile Leu Leu
            20                  25                  30

Phe Ile Ile Thr Leu Phe Leu Leu Ile Val Gly Leu Tyr Ile Ala Asn
        35                  40                  45

Ser Leu Ala Tyr Ala Arg Phe Ala Ser Thr Ser Thr Gly Pro Ile Ala
    50                  55                  60

Ala Pro Asp Val Thr Lys Cys Gly Gln Pro Asp Leu Pro Pro Gly Thr
65                  70                  75                  80

Ala Pro Ile Asn Cys Cys Pro Pro Ile Pro Ala Lys Ile Ile Asp Phe
                85                  90                  95

Glu Leu Pro Pro Pro Ser Thr Thr Met Arg Val Arg Arg Ala Ala His
            100                 105                 110

Leu Val Asp Asp Ala Tyr Ile Ala Lys Phe Lys Lys Ala Val Glu Leu
        115                 120                 125

Met Arg Ala Leu Pro Glu Asp Asp Pro Arg Ser Phe Lys Gln Gln Ala
    130                 135                 140

Asn Val His Cys Ala Tyr Cys Ala Gly Ala Tyr Asn Gln Ala Gly Phe
145                 150                 155                 160

Thr Asn Leu Lys Leu Gln Ile His Arg Ser Trp Leu Phe Phe Pro Phe
                165                 170                 175

His Arg Tyr Tyr Ile Tyr Phe Phe Glu Arg Ile Leu Gly Lys Leu Ile
            180                 185                 190

Asn Asp Thr Thr Phe Ala Leu Gln Phe Trp Asn Tyr Asp Ser Pro Gly
        195                 200                 205

Gly Met Thr Ile Pro Ser Met Phe Ile Asp Thr Asn Ser Ser Leu Tyr
    210                 215                 220

Asp Ser Leu Arg Asp Ser Asn His Gln Pro Thr Ile Val Asp Leu
225                 230                 235                 240

Asn Tyr Ala Phe Ser Asp Ser Asp Asn Thr Thr Thr Pro Glu Glu Gln
                245                 250                 255

Met Ile Ile Asn Leu Lys Ile Val Tyr Arg Gln Met Val Ser Ser Ala
            260                 265                 270

Lys Thr Pro Gln Leu Phe Gly Arg Pro Tyr Arg Arg Gly Asp Gln
        275                 280                 285
```

```
Glu Phe Pro Gly Val Gly Ser Ile Glu Leu Val Pro His Gly Met Ile
    290                 295                 300

His Leu Trp Thr Gly Ser Glu Asn Thr Pro Tyr Gly Glu Asn Met Gly
305                 310                 315                 320

Ala Phe Tyr Ser Thr Ala Arg Asp Pro Ile Phe Phe Ala His His Ser
                325                 330                 335

Asn Val Asp Arg Met Trp Ser Ile Trp Lys Thr Leu Gly Gly Pro Arg
            340                 345                 350

Arg Thr Asp Leu Thr Asp Pro Asp Phe Leu Asp Ala Ser Phe Val Phe
        355                 360                 365

Tyr Asp Glu Asn Ala Glu Met Val Arg Val Lys Val Arg Asp Cys Leu
    370                 375                 380

Asp Glu Lys Lys Leu Gly Tyr Val Tyr Gln Asp Val Glu Ile Pro Trp
385                 390                 395                 400

Leu Asn Thr Arg Pro Thr Pro Lys Val Ser Pro Ser Leu Leu Lys Lys
                405                 410                 415

Phe His Arg Thr Asn Thr Ala Asn Pro Arg Gln Val Phe Pro Ala Ile
            420                 425                 430

Leu Asp Arg Val Leu Lys Val Ile Val Thr Arg Pro Lys Lys Thr Arg
        435                 440                 445

Ser Arg Lys Glu Lys Asp Glu Leu Glu Glu Ile Leu Val Ile Glu Gly
    450                 455                 460

Ile Glu Leu Glu Arg Asp His Gly His Val Lys Phe Asp Val Tyr Ile
465                 470                 475                 480

Asn Ala Asp Glu Asp Asp Leu Ala Val Ile Ser Pro Glu Asn Ala Glu
                485                 490                 495

Phe Ala Gly Ser Phe Val Ser Leu Trp His Lys Pro Ile Lys Gly Lys
            500                 505                 510

Arg Thr Lys Thr Gln Leu Leu Thr Leu Ser Ile Cys Asp Ile Leu Glu
        515                 520                 525

Asp Leu Asp Ala Asp Glu Asp Asp Tyr Val Leu Val Thr Leu Val Pro
    530                 535                 540

Arg Asn Ala Gly Asp Ala Ile Lys Ile His Asn Val Lys Ile Glu Leu
545                 550                 555                 560

Asp Gly

<210> SEQ ID NO 3
<211> LENGTH: 13
<212> TYPE: PRT
<213> ORGANISM: Antirrhinum majus

<400> SEQUENCE: 3

Lys Lys Leu Gly Tyr Val Tyr Gln Asp Val Glu Ile Pro
1               5                   10

<210> SEQ ID NO 4
<211> LENGTH: 12
<212> TYPE: PRT
<213> ORGANISM: Antirrhinum majus

<400> SEQUENCE: 4

Lys Ile Val Tyr Arg Gln Met Val Ser Ser Ala Lys
1               5                   10

<210> SEQ ID NO 5
<211> LENGTH: 18
```

```
<212> TYPE: PRT
<213> ORGANISM: Antirrhinum majus

<400> SEQUENCE: 5

Lys Thr Pro Gln Leu Phe Phe Gly Arg Pro Tyr Arg Arg Gly Asp Gln
1               5                   10                  15

Glu Phe

<210> SEQ ID NO 6
<211> LENGTH: 30
<212> TYPE: PRT
<213> ORGANISM: Antirrhinum majus
<220> FEATURE:
<221> NAME/KEY: UNSURE
<222> LOCATION: (8)..(8)
<223> OTHER INFORMATION: Amino acid 8 is Xaa wherein Xaa = unknown or
      other.
<220> FEATURE:
<221> NAME/KEY: UNSURE
<222> LOCATION: (28)..(28)
<223> OTHER INFORMATION: Amino acid 28 is Xaa wherein Xaa = unknown or
      other.

<400> SEQUENCE: 6

Lys Ile Ile Asp Phe Glu Leu Pro Xaa Pro Ser Thr Thr Met Arg Val
1               5                   10                  15

Arg Arg Ala Ala His Leu Val Asp Asp Ala Tyr Ile Xaa Lys
            20                  25                  30

<210> SEQ ID NO 7
<211> LENGTH: 125
<212> TYPE: PRT
<213> ORGANISM: Antirrhinum majus

<400> SEQUENCE: 7

Arg Gln Met Val Ser Ser Ala Lys Thr Pro Gln Leu Phe Phe Gly Arg
1               5                   10                  15

Pro Tyr Arg Arg Gly Asp Gln Glu Phe Pro Gly Val Gly Ser Ile Glu
            20                  25                  30

Leu Val Pro His Gly Met Ile His Leu Trp Thr Gly Ser Glu Asn Thr
        35                  40                  45

Pro Tyr Gly Glu Asn Met Gly Ala Phe Tyr Ser Thr Ala Arg Asp Pro
    50                  55                  60

Ile Phe Phe Ala His His Ser Asn Val Asp Arg Met Trp Ser Ile Trp
65                  70                  75                  80

Lys Thr Leu Gly Gly Pro Arg Arg Thr Asp Leu Thr Asp Pro Asp Phe
                85                  90                  95

Leu Asp Ala Ser Phe Val Phe Cys Asp Glu Asn Ala Glu Met Val Arg
            100                 105                 110

Val Lys Val Arg Asp Cys Leu Asp Gly Lys Lys Leu Gly
        115                 120                 125

<210> SEQ ID NO 8
<211> LENGTH: 7
<212> TYPE: PRT
<213> ORGANISM: Artificial Sequence
<220> FEATURE:
<223> OTHER INFORMATION: Primer
<220> FEATURE:
<221> NAME/KEY: PEPTIDE
<222> LOCATION: (2)..(2)
<223> OTHER INFORMATION: Amino acid 2 is Xaa wherein Xaa = Val or Ile.

<400> SEQUENCE: 8
```

```
Phe Xaa Lys Phe Thr Ala Ile
1               5
```

<210> SEQ ID NO 9
<211> LENGTH: 6
<212> TYPE: PRT
<213> ORGANISM: Artificial Sequence
<220> FEATURE:
<223> OTHER INFORMATION: Primer
<220> FEATURE:
<221> NAME/KEY: PEPTIDE
<222> LOCATION: (6)..(6)
<223> OTHER INFORMATION: Amino acid 6 is Xaa wherein Xaa = Thr or Pro.

<400> SEQUENCE: 9

```
Lys Trp Lys Gly Lys Xaa
1               5
```

<210> SEQ ID NO 10
<211> LENGTH: 6
<212> TYPE: PRT
<213> ORGANISM: Artificial Sequence
<220> FEATURE:
<223> OTHER INFORMATION: Primer

<400> SEQUENCE: 10

```
His Ala Val Cys Asn Glu
1               5
```

<210> SEQ ID NO 11
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(18)
<223> OTHER INFORMATION: Nucleotides 6, 15 and 18 are "n" wherein
      "n" = a or c or g or t/u or unknown or other

<400> SEQUENCE: 11
ttyrtnaart tyacngcnat                                              20

<210> SEQ ID NO 12
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: Nucleotide 12 is "n" wherein "n" = a or c or
      g or t/u or unknown or other

<400> SEQUENCE: 12
aartggaarg gnaarmc                                                 17

<210> SEQ ID NO 13
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(7)

-continued

```
<223> OTHER INFORMATION: Nucleotides 4 and 7 are "n" wherein "n" = a or
      c or g or t/u or unknown or other

<400> SEQUENCE: 13
rtgngcnacr carttytc                                               18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
aaggatccgg ccctatcgcc                                             20

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gggttcgaag aattcatctc tg                                          22
```